United States Patent [19]
Chen et al.

[11] Patent Number: 4,879,905
[45] Date of Patent: Nov. 14, 1989

[54] APPARATUS FOR MEASURING THE INTERNAL FRICTION OF A TRANVERSELY VIBRATING METAL SPECIMEN

[75] Inventors: Hong-Bin Chen; Lien-Kuei Chang; Shern-Ji Tsay; Tung-Sheng Chou, all of Kaohsiung; Fong Shiue, Taipei, all of Taiwan

[73] Assignee: China Steel Corporation, Haohsiung, Taiwan

[21] Appl. No.: 255,872

[22] Filed: Oct. 11, 1988

[51] Int. Cl.[4] ............................................. G01N 29/00
[52] U.S. Cl. ......................................... 73/579; 73/576
[58] Field of Search ................. 73/570, 571, 574, 576, 73/579, 763, 766; 374/52, 50

[56] References Cited

U.S. PATENT DOCUMENTS

| | | | |
|---|---|---|---|
| 3,623,358 | 11/1971 | Sugimoto | 73/579 |
| 4,018,080 | 4/1977 | Fletcher et al. | 374/50 |
| 4,231,259 | 11/1980 | Thiruvengadam | 73/584 |
| 4,794,798 | 1/1989 | Matsushita et al. | 73/789 |

FOREIGN PATENT DOCUMENTS

| | | | |
|---|---|---|---|
| 259931 | 12/1985 | Japan | 73/763 |
| 182382 | 5/1966 | U.S.S.R. | 73/576 |

OTHER PUBLICATIONS

"An Apparatus for Measuring Internal Friction of Films During the Process of Plastic Deformation in the Temperature Range from 4.2 to 300 K", by V. S. Postnikov et al., Cryogenics, vol. 19, No. 2, Feb. 1979.

Primary Examiner—John Chapman
Assistant Examiner—Louis M. Arana
Attorney, Agent, or Firm—Ladas & Parry

[57] ABSTRACT

A measuring apparatus is provided for measuring the internal friction of a transversely vibrating metal specimen at various operation temperatures. The measuring apparatus includes a container body mounted on a machine table and having an open upper end, an ascending device for moving vertically a container lid into and out of engagement with the container body, and a measuring unit secured to the lower surface of the container lid. The measuring unit includes a measuring rack, a heating body, a heating source, a temperature sensing element, a water-cooled driving member and a water-cooled detecting member. The specimen can be driven by the driving member to vibrate in the measuring unit and detected by the detecting member to allow determination of its metal properties.

5 Claims, 10 Drawing Sheets

APPARATUS FOR MEASURING THE INTERNAL FRICTION OF A TRANVERSELY VIBRATING METAL SPECIMEN

BACKGROUND OF THE INVENTION

This invention relates to a testing equipment, and more particularly to an apparatus for measuring the internal friction of a metal specimen.

The technique of measuring the internal friction of a metal specimen is important in the study of metal. In particular, the internal friction measurement is the only exsisting method which can be used to determine the solute content of carbon and/or nitrogen in steel. There are two major conventional methods for measuring the internal-friction behavior. The first one is the torsion pendulum method in which one end of a metal specimen is hung so that it can be driven to cause torsional vibration. The amplitude of the vibration, after reaching a certain value, is then freely reduced. The amplitude attenuation of the vibration vs. temperature and some internal friction peaks can be obtained, with which many characteristics, such as point defects, dislocations, and grain boundaries of the metal, the distribution and diffusion parameters of some elements in an alloy, and so on may be investigated. The other method is the transverse vibration method in which a metal specimen is driven to cause a transverse vibration of the specimen. The amplitude of its transverse vibration, after reaching a certain value, is also freely reduced.

Figure 1:
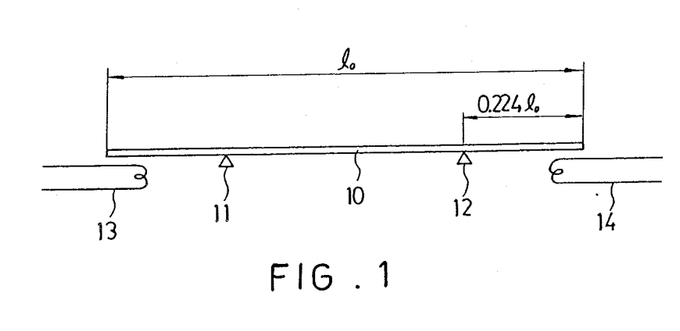
FIG. 1 is a schematic view illustrating an internal friction test for a metal specimen.

Referring to FIG. 1, a metal specimen 10 is placed on two spaced-apart supporting points 11 and 12 in a transverse vibration internal friction measurement. A drive means 13 which is usually a magnetic coil 13 being disposed near one end of the specimen 10. A detecting coil 14 is disposed near the other end of the specimen 10. The driving coil 13 and the detecting coil 14 may be replaced with electrostatic exciting and detecting devices.

Figure 2:
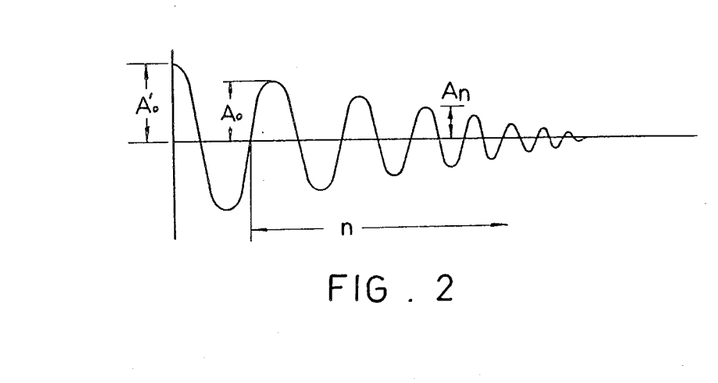
FIG. 2 is a wave form graph obtained from the internal friction test of FIG. 1.

The internal friction is represented by $\theta^{-1}$ and can be obtained from the following equation;

$$\theta^{-1} = \frac{1}{n\pi} l_o \frac{A_o}{A_n}$$

where $A_o$ and $A_n$ are the starting and final amplitudes of free vibration decay in the calculation, respectively. In FIG. 2, $A'_o$, although does not exist in the equation, is the very begining amplitude of free vibration decay.

Figure 3:
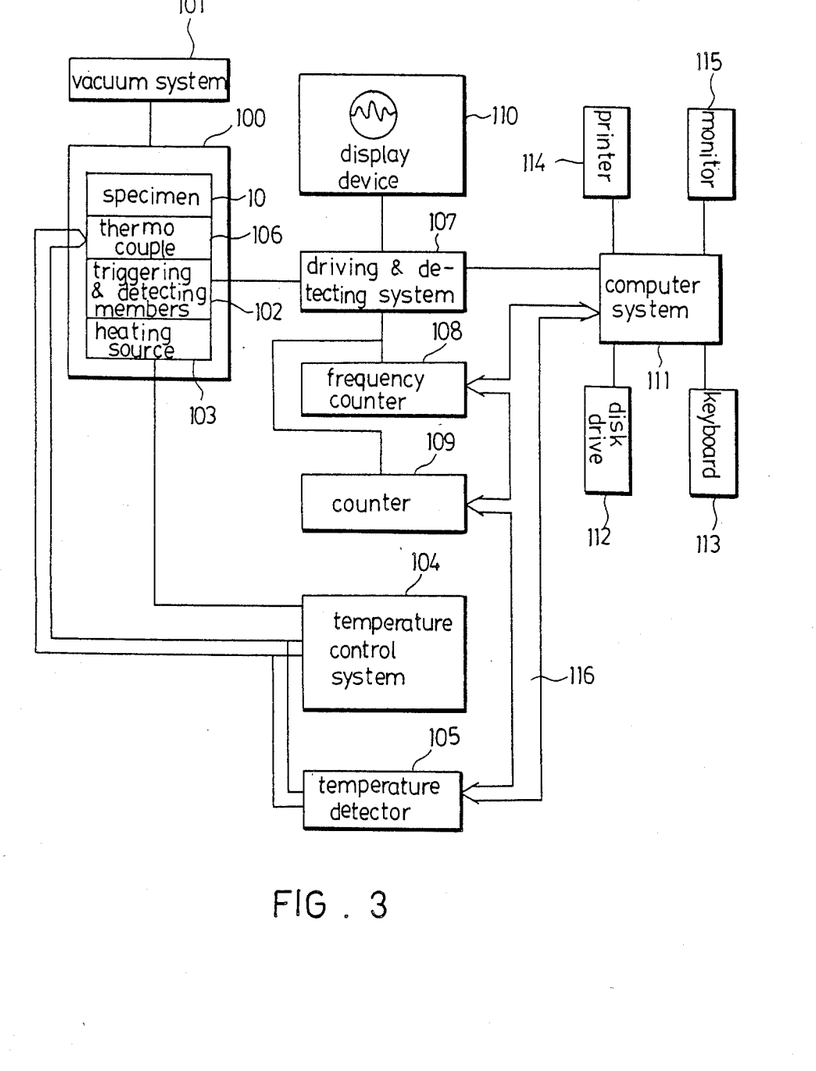
FIG. 3 is a block diagram of a transverse vibration internal friction measuring system.

FIG. 3 is a block diagram of a transverse vibration friction measuring system which includes a measuring apparatus 100. A vacuum is formed in the measuring apparatus 100 by a vacuum system 101. This vacuum is necessary for the proper measurement of a metal specimen 10. An assembly 102 of a driving member and a detecting member, a temperature sensing element 106 and a heating source 103 are mounted within the measuring apparatus 100. Normally, the temperature sensing element 106 is a thermocouple. The operation of the heating source 103 is controlled by a programmable temperature automatic control system 104 so as to provide an appropriate heating rate and final temperature to the measuring system. The temperature control system 104 is connected to a temperature detector 105 which can detect the ambient temperature of the specimen 10 by the temperature sensing element 106. The measuring system also includes a driving and detecting system 107 supervised by a frequency counter 108 which can provide cycle force of resonant frequency of the specimen. A counter 109 is used to count the number of the transverse vibration decay from amplitude $A_o$ to $A_n$ of the specimen 10. A display device 110 which is an oscilloscope is used to display the wave form of the transverse vibration of the specimen 10. The measuring system is equipped with a digital analysis computer system 111 which includes a disk drive 112, a keyboard 113, a printer 114 and a monitor 115. The computer system 111 is connected to the frequency counter 108, the counter 109 and the temperature detector 105 by a data bus 116 so as to analyze and calculate the vibration information of the specimen 10. The computer system 111 also control the starting of the driving and detecting unit 107 and can determine the operation time and temperature of the driving and detecting process so as to obtain the internal friction vs. temperature and the elastic modulus-temperature curves which help to understand the type of the internal friction peaks of the specimen 10.

Conventional internal friction measuring systems have disadvantage in that the specimen 10 is difficult to conveniently and accurately mount in the measuring apparatus 100. In addition, the assembly 102 of the driving member and the detecting member may burn down at a high temperature.

SUMMARY OF THE INVENTION

It is therefore the main object of this invention to provide an internal friction measuring apparatus in which the metal specimen can be mounted conveniently and accurately.

Another object of this invention is to provide an internal friction measuring apparatus in which the electro-magnetic coils of the driving member and the detecting member can work at a high temperature of about 400° C.

According to this invention, a measuring apparatus is provided for measuring the internal friction of a metal specimen. The measuring apparatus includes a machine table, a container body fixed on the machine table and having an open upper end, and a container lid covering the upper end of the container body. An ascending device carries the container lid thereon for moving vertically the container lid into and out of engagement with the container body. A measuring unit is carried on the lower surface of the container lid and can be moved downward into the container body when the container lid engages with the container body. The specimen can be vibrated transversely in the measuring unit in such a manner that the amplitude of the transverse vibration, after reaching a certain value, is freely decayed. The measuring unit includes a driving member having a channel formed therein; a detecting member spaced apart from the driving member and having a channel formed in the detecting member; a cold water feeding pipe communicated with both the channels of the driving member and the detecting member; and a drain pip also communicated with both the channels of the driving member and the detecting member. The measuring unit further includes a heating body formed in the unit's upper surface with a groove, and a measuring rack placed removably within the groove of the heating body and adapted for the placement of the specimen on the measuring rack.

BRIEF DESCRIPTION OF THE DRAWINGS

Other features and advantages of this invention will become apparent in the following detailed description of a preferred embodiment of this invention with reference to the accompanying drawings in which.

DETAILED DESCRIPTION OF THE PREFERRED EMBODIMENT

Figure 4:
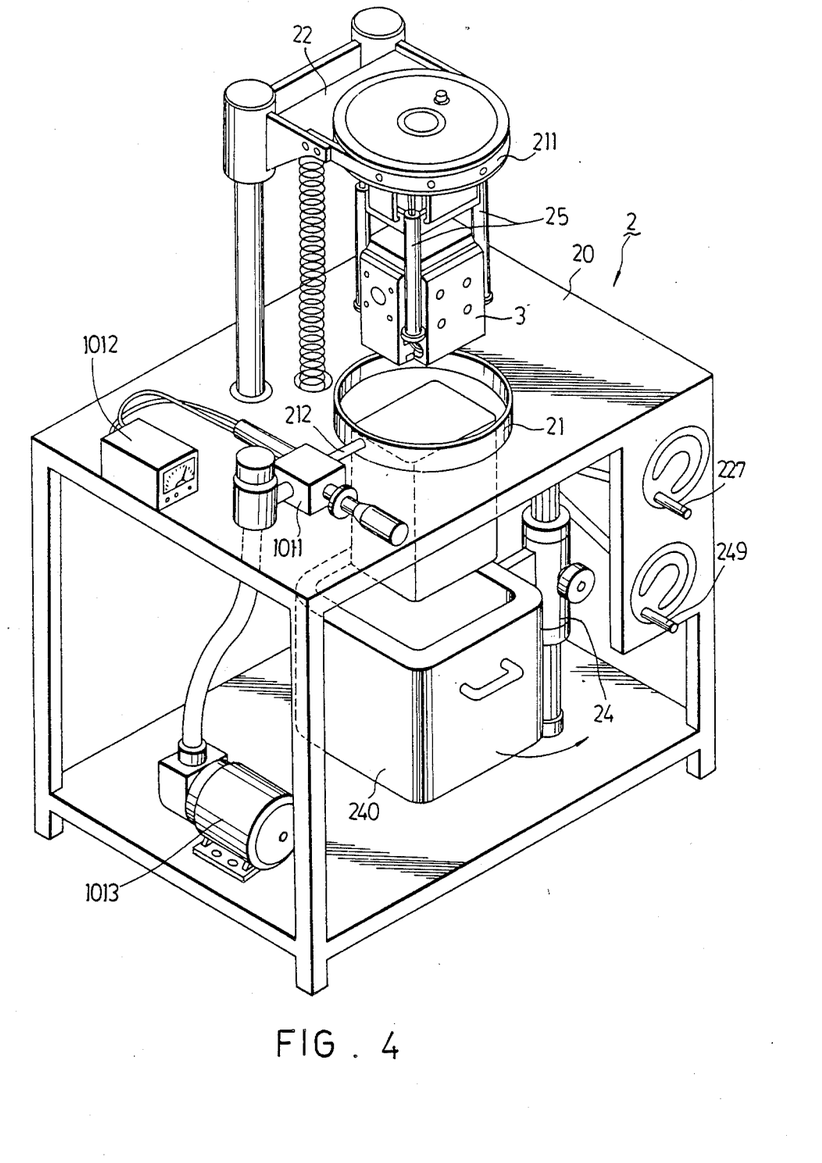
FIG. 4 is a perspective view of an internal friction measuring apparatus according to this invention.

Referring to FIG. 4, a transverse vibration internal friction measuring apparatus 2 is shown. The measuring apparatus 2 includes a machine table 20 on which a container body 21 is fixed. The container body 21 is open at the upper end thereof. A container lid 211 is carried on a container lid ascending device 22 which is mounted on the machine table 20 so that the container lid 211 can be moved vertically by the ascending device 22 into or out of engagement with the open upper end of the container body 21. When the container lid 211 engages with the container body 21, the container body 21 is closed. The container body 21 is connected to a conventional vacuum system which includes a control valve 1011, a vacuum display means 1012 and a vacuum pump 1013 so as to form a vacuum in the measuring apparatus 2, thereby offering stable operation surroundings. A vessel ascending device 24 is also mounted on the machine table 20 and carries a low-temperature vessel 240 thereon just below the container body 21. The vessel 240 has an open upper end and is filled with a low-temperature liquid, such as liquefied nitrogen. The vessel 240 can be moved upward by the vessel ascending drive 24 so that the lower portion of the container body 21 is dipped into the liquid in the vessel 240, thereby creating lowtemperature operation surroundings. A measuring unit 3 is connected securely to the lower surface of the container lid 211 by four support rods 25 so that when the container lid 211 is moved downward by the container lid ascending device 22 to close the upper end of the container body 21, the measuring unit 3 is positioned within the container body 21.

Figure 5:
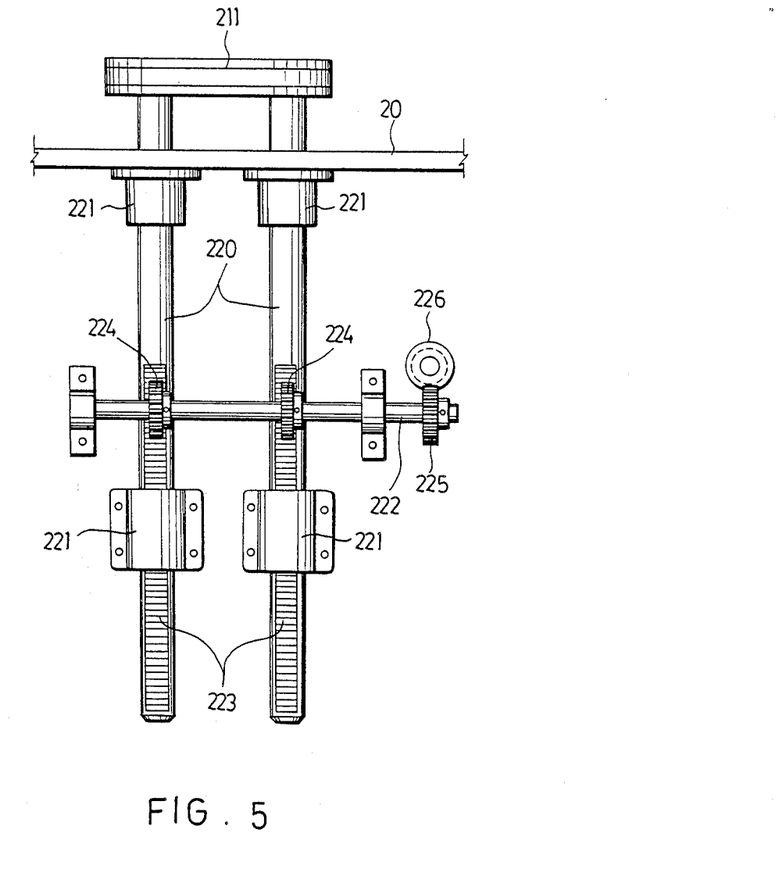
FIG. 5 is a schematic view illustrating the container lid ascending device of the measuring apparatus according to this invention.

Referring to FIG. 5, the container lid ascending device 22 includes two parallel upright slide rods 220 each inserted slidably through two spaced-apart guides 221 which are fixed on the machine table 20. The container lid 211 is carried on the upper ends of the slide rods 220. Each of the slide rods 220 is provided at the lower portion thereof with a rack 223 which engages with the pinion 224 of a drive shaft 222 which is rotated by a driving assembly which includes interengaged worm gear 225 and worm 226. When rotating a first swing arm 227 (see FIG. 4) to drive the worm 226, the drive shaft 222 rotates to ascend or descend the slide rods 220 and hence the container lid 211. Certainly, the container lid ascending device 22 may be replaced with any other conventionaly ascending device.

Figure 6:
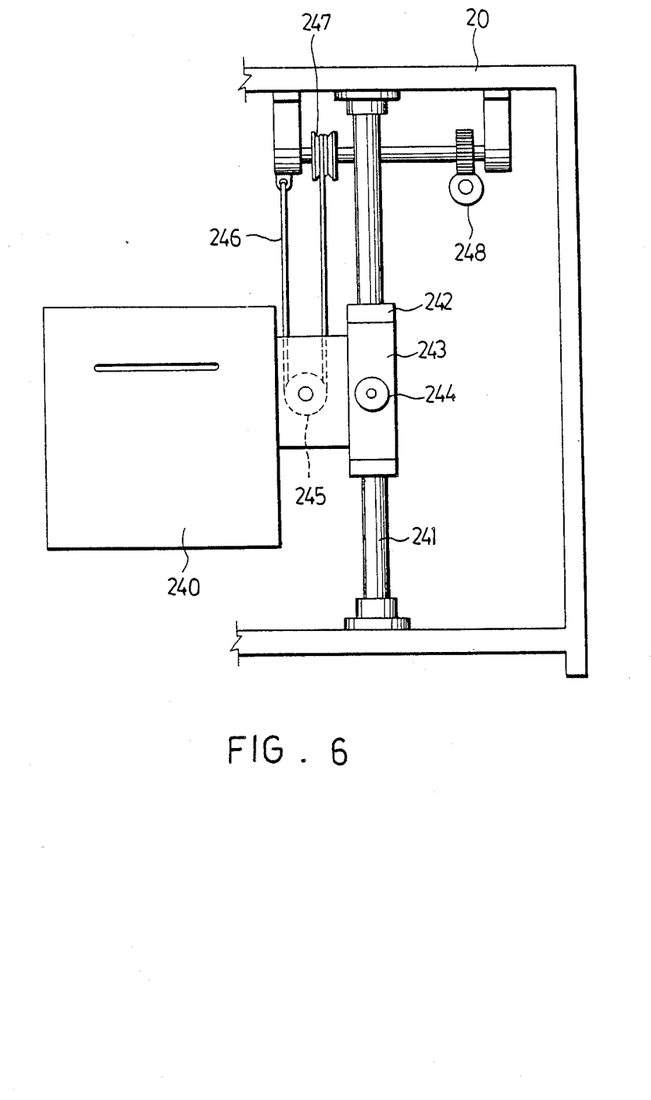
FIG. 6 is a schematic view illustrating a movable vessel ascending device of the measuring apparatus according to this invention.

Referring to FIG. 6, the vessel ascending device 24 includes an externally splined guide rod 241, and an internally splined slide 242 sleeved slidably on the guide rod 241. A tubular rotating member 243 is sleeved rotatably on the slide 242 and locked on the slide 242 by a locking bolt 244. The vessel 240 is connected securely to the rotating member 243 by a connecting plate on which a pulley 245 is mounted. When the locking bolt 244 is loosened, the rotating member 243 and hence the vessel 240 can rotate relative to the slide 242. A cable 246 extends around the pulley 245 and is fastened to the machine table 20 at an end thereof. The cable 246 is wound on a winch 247 which is sleeved rigidly on a rotating shaft. The rotating shaft is driven by a driving assembly which includes interengaged worm gear and worm 248 which can be rotated by a second swing arm 249 (see FIG. 4). The vessel ascending device 24 may also be replaced with any other conventional ascending device. When it is desired to cool the container body 21, the vessel 240 can be moved upward so that the container body 21 is dipped into the liquid in the vessel 240. When it is desired to implement the low-temperature liquid into the vessel 240, the vessel 240 can be moved downward away from the container body 21 and turned outward in the direction indicated by the arrow in FIG. 4.

Figure 7:
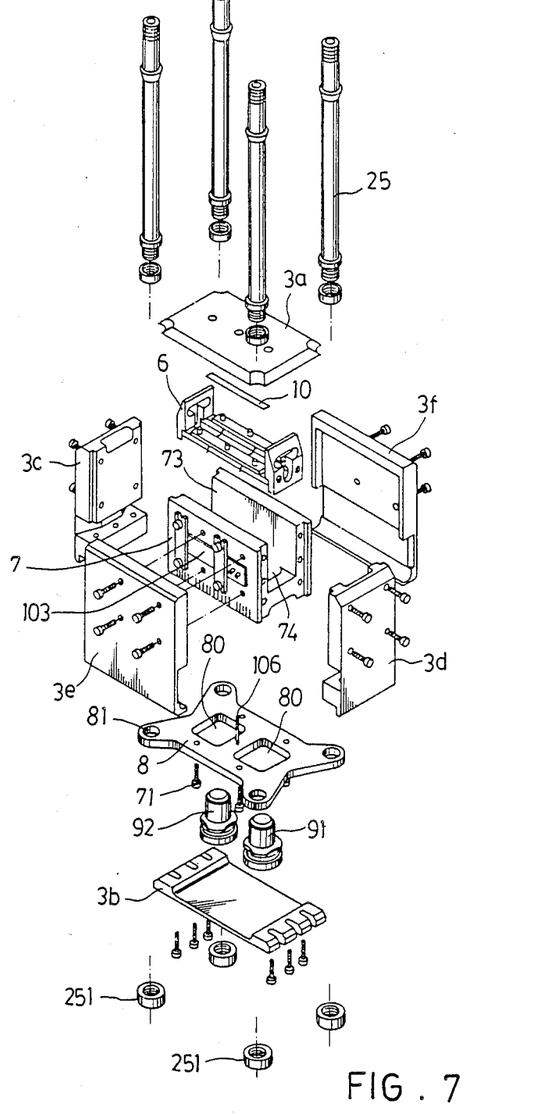
FIG. 7 is an exploded view showing the measuring unit of the measuring apparatus according to this invention.
Figure 9:
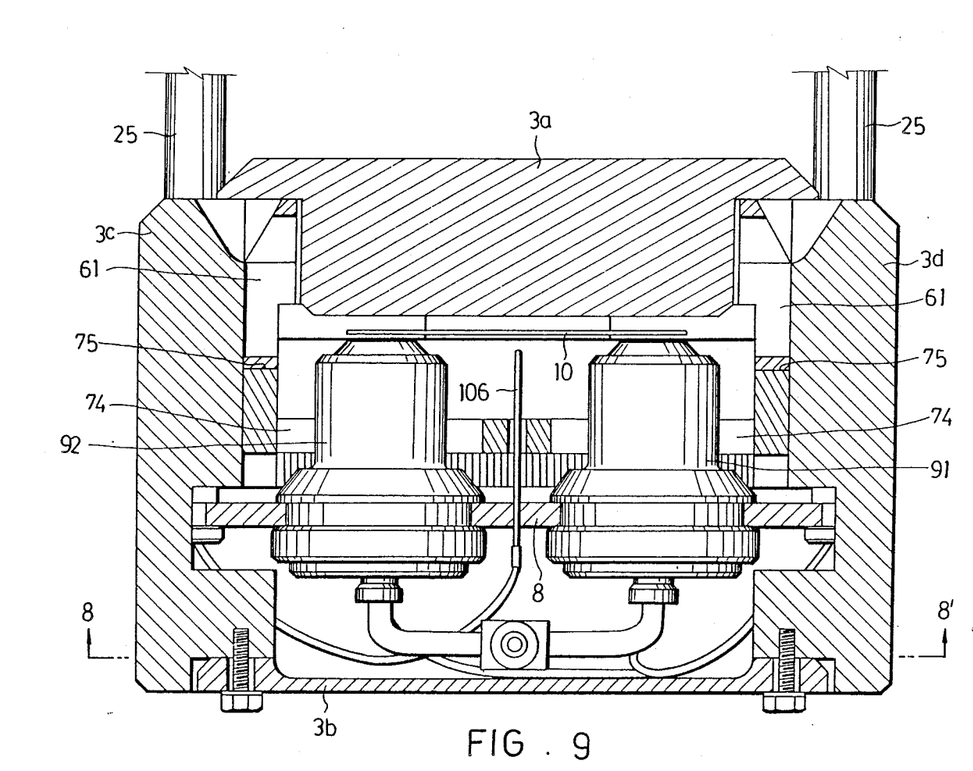
FIG. 9 is a sectional view showing the measuring unit of the measuring apparatus according to this invention.

Referring to FIGS. 7 and 9, the measuring unit 3 includes a base plate 8 which has four circular holes 81 in its periphery. The remaining parts of the measuring unit 3 are attached to the base plate 8, as described hereinafter. Each of the support rods 25 has an externally threaded lower end which extends through the corresponding circular hole 81 of the base plate 8 to engage with a nut 251 so that the measuring unit 3 is carried on the support rods 25. The base plate 8 includes a thermocouple 106 installed on the center thereof, and two rectangular holes 80 formed in the base plate 8 on the opposite sides of the thermocouple 106 for the insertion of a driving member 91 and a detecting member 92 into the rectangular holes 80. A heating body 7 is fastened to the upper surface of the base plate 8 by bolts 71 and has a groove 73 formed in the upper surface thereof for the placement of a measuring rack 6. Heating sources 103 are secured to the outer surfaces of the side walls of the heating body 7. Two holes 74 are formed in the bottom wall of the heating body 7 in alignment with the rectangular holes 80 of the base plate 8 so that the driving member 91 and the detecting member 92 can be positioned near a metal specimen 10 which is placed on the measuring rack 6. Four heat dissipating side plates 3c, 3d, 3e and 3f are screwed to the side walls of the heating body 7. A heat dissipating bottom plate 3b is screwed to the bottom surfaces of the side plates 3c, 3d, 3e and 3f. A heat dissipating top plate 3a is placed on the upper surfaces of the side plates 3c, 3d, 3e and 3f and is provided at its corners with four curved notches which engage with the support rods 25. Because the measuring rack 6, heating body 7, base plate 8, driving member 91, and detecting member 92 are enclosed by the heat dissipating plates 3a–f, the operation temperature of the specimen 10 can be adjusted rapidly and controlled desirably.

Figure 8:
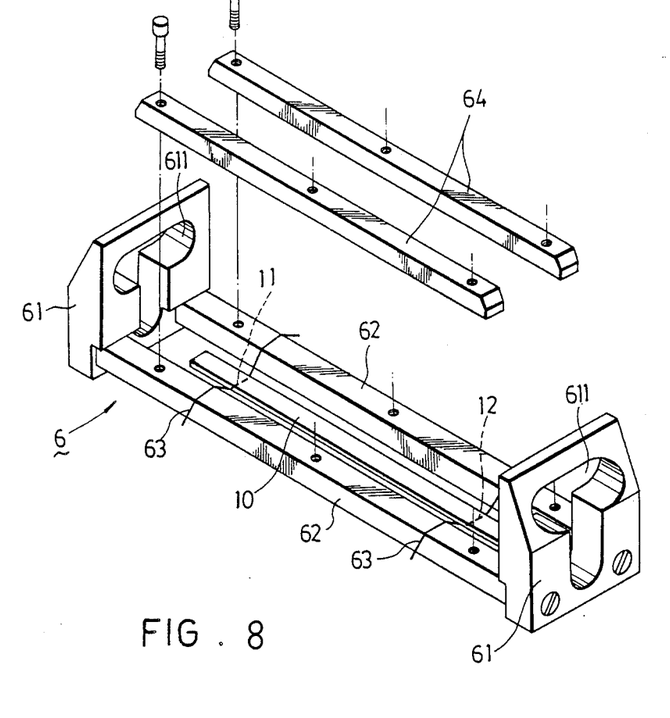
FIG. 8 is a perspective view showing the measuring rack of the measuring apparatus according to this invention.

Referring to FIG. 8, the measuring rack 6 includes two bases 61 each of which has a generally T-shaped cutout 611 so that a grip is formed at the upper end portion of each of the bases 61. Each of the two parallel beams 62 is screwed to the bases 61. The beams 62 are spaced apart from each other so as to form a space for accommodating the specimen 10. Each of two bridging wires 63 bridges the beams 62 in such a manner that the intermediate portion of the wire 63 is curved to form a general U-shape. Two pressing levers 64 are screwed to the upper surfaces of the beams 62 respectively to press the wires 63 of the beams 62. As a result, the intermediate portions of the wires 63 can swing between the beams 62. When the specimen 10 bridges the intermediate portions of the wires 63, the wires 63 serve as supporting points so that the specimen 10 can be driven to vibrate between the beams 62. As shown in FIG. 9, because the measuring rack 6 is sized in conformity with the groove 73 of the heating body 7, it is positioned accurately on the bottom wall 75 of the heating body 7. When the container lid 211 and the measuring unit 3 are moved upward out of the container body 21 by the container lid ascending device 22 and the heat dissipating top plate 3a is removed from the measuring unit 3, the specimen 10 can be placed conveniently and accurately into the measuring unit 3.

Figure 10:
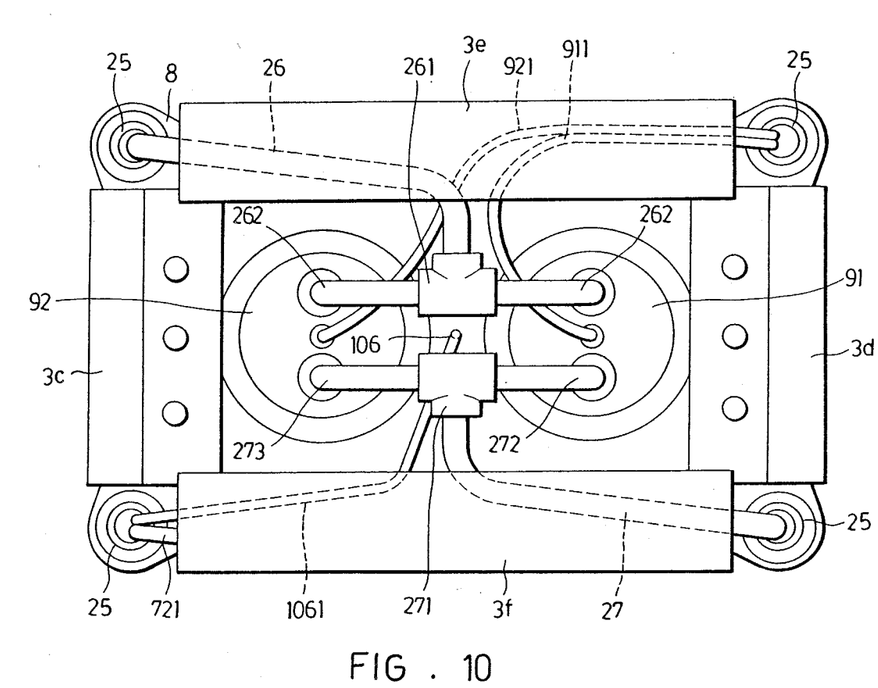
FIG. 10 is a view taken along the line 8—8 in FIG. 9.

Referring to FIG. 10, electrical wires 721, 1061, 911 and 921 are respectively connected to the heating sources 103, thermocouple 106, driving member 91 and detecting member 92 and extend through the open-ended slots of the side plates 3e and 3f and the support rods 25 to connect the programmable temperature control system 104, temperature detector 105 and driving and detecting system 107, which are shown in FIG. 3. A cold water feeding pipe 26 and a drain pipe 27 also extend through the support rods 25. A first three-way pipe 261 allows the cold water feeding pipe 26 to communicate with two first conducts 262 and 263 which extend into the driving member 91 and the detecting member 92 respectively. Similarly, a second three-way pipe 271 allows the drain pipe 27 to communicate with two second conducts 272, 273 which extend into the driving member 91 and the detecting member 92 respectively. This allows cold water to flow through the driving member 91 and the detecting member 92 providing a cooling effect.

Figure 11:
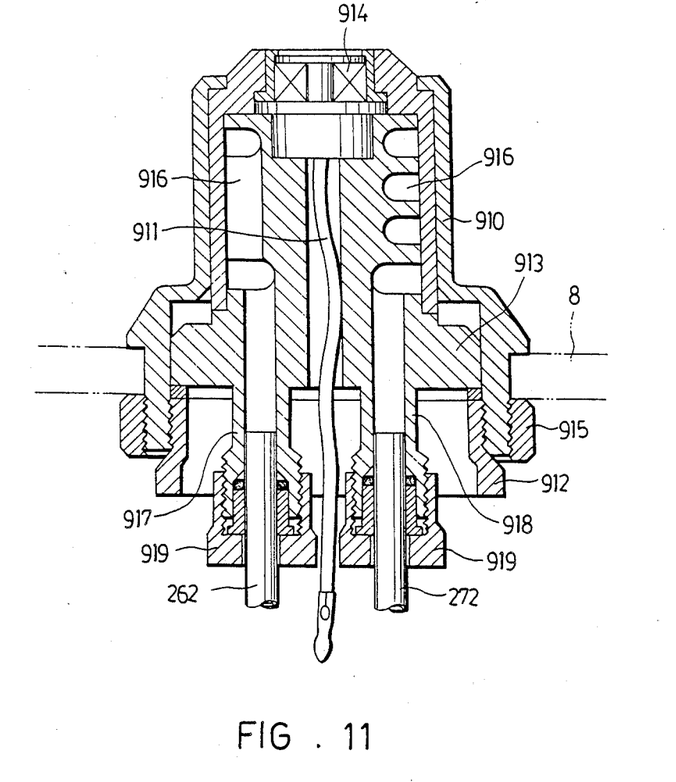
FIG. 11 is a sectional view showing the driving member of the measuring apparatus according to this invention.

The driving member 91 and the detecting member 92 are similar to each other in construction. Referring to FIG. 11, the driving member 91 includes a tubular housing 910 which has an outward flange at its intermediate portion, and an externally threaded lower end allowing it to be fastened to the base plate 8 by a nut 915. The lower end of the tubular housing 910 is also internally threaded so that a driving body 913 can be confined within the tubular housing 910 by engaging an externally threaded retaining ring 912 with the internal threads of the tubular housing 910. A driving source 914 which is typically a coil, is exposed to the top surface of the driving member 91 and powered by an electrical wire 911 which extends through the driving member 91.

The driving body 913 has a cold water channel 916 which is communicated with both the first conduct 262 and the second conduct 272 by adapters 919. The interior of the driving member 91 therefore permits a relatively high temperature though not high enough to cause the driving member 91 to burn down. In turn, this compulsory water-cooled arrangement can increase the operation tempeature of the specimen 10.

With this invention thus explained, it is apparent that numerous modifications and variations can be made without departing from the scope and spirit of this invention. It is therefore intended that this invention be limited only as indicated in the appended claims.

We claim:

1. A measuring apparatus for measuring internal friction of a metal specimen comprising:
   a machine table;
   a container including a container body fixed on said machine table and having an open upper end, and a container lid covering said upper end of said container body;
   an ascending device carrying said container lid thereon for moving vertically said container lid into and out of engagement with said container body, said container lid covering said container body when one is engaged with the other; and
   a measuring unit carried on a lower surface of said container lid and movable into said container body when said container lid engages with said container body, said measuring unit including a driving member having a channel formed therein for causing the specimen to vibrate for the purpose of measuring internal friction, a detecting member spaced apart from said driving member and having a channel formed in said detecting member for detecting the vibrations in the specimen, a cold water feeding pipe communicating with both said channels of said driving member and said detecting member, and a drain pipe also communicating with both said channels of said driving member and said detecting member.

2. A measuring apparatus as claimed in claim 1, wherein said measuring unit includes a heating body means having connected side walls to form a groove therebetween, and a measuring rack placed removably within said groove of said heating body means and adapted for placement of said specimen on said measuring rack.

3. A measuring apparatus as claimed in claim 2, wherein said measuring rack includes:
   two opposed bases spaced apart from each other;
   two parallel beams interconnected securely between said bases; and
   two parallel bridging wires each bridging said beams in such a manner that intermediate portions of said wires can swing between said beams;
   whereby, said specimen can bridge said swingable intermediate portions of said wires so that said specimen can be driven to vibrate between said beams.

4. A measuring apparatus as claimed in claim 3, wherein each of said bases has a grip secured thereto so that operator can conveniently hold said measuring rack.

5. A measuring apparatus as claimed in claim 3, wherein said measuring rack includes two pressing levers which respectively press ends of said wires onto upper surfaces of said beams.

* * * * *